United States Patent
Foerster et al.

(10) Patent No.: US 8,579,901 B1
(45) Date of Patent: Nov. 12, 2013

(54) SUTURE BAND BUCKLE AND METHODS

(75) Inventors: Seth Arnold Foerster, San Clemente, CA (US); David Trottingwolf Aldridge, Laguna Hills, CA (US)

(73) Assignee: Dallen Medical, Inc., San Clemente, CA (US)

( * ) Notice: Subject to any disclaimer, the term of this patent is extended or adjusted under 35 U.S.C. 154(b) by 316 days.

(21) Appl. No.: 12/815,989

(22) Filed: Jun. 15, 2010

Related U.S. Application Data (60) Provisional application No. 61/187,846, filed on Jun. 17, 2009.

(51) Int. Cl.
*A61B 17/82* (2006.01)
*A61B 17/56* (2006.01)

(52) U.S. Cl.
USPC .......................................................... 606/74

(58) Field of Classification Search
USPC .................. 606/74, 232, 233, 139–151, 228; 24/168, 171, 194, 196
See application file for complete search history.

(56) References Cited

U.S. PATENT DOCUMENTS

| | | | |
|---|---|---|---|
| 303,360 A | 8/1884 | Brunner | |
| 3,822,445 A | 7/1974 | Feng | |
| 4,279,248 A | 7/1981 | Gabbay | |
| 4,444,181 A | 4/1984 | Wevers et al. | |
| 4,535,772 A | 8/1985 | Sheehan | |
| 4,608,735 A * | 9/1986 | Kasai | 24/196 |
| 4,667,675 A | 5/1987 | Davis | |
| 4,730,615 A | 3/1988 | Sutherland et al. | |
| 4,813,416 A * | 3/1989 | Pollak et al. | 606/151 |
| 4,901,721 A | 2/1990 | Hakki | |
| 4,938,760 A | 7/1990 | Burton et al. | |
| 4,959,064 A | 9/1990 | Engelhardt | |
| 4,969,892 A | 11/1990 | Burton et al. | |
| 5,123,153 A * | 6/1992 | Krauss | 24/196 |
| 5,330,489 A * | 7/1994 | Green et al. | 606/151 |
| 5,339,870 A * | 8/1994 | Green et al. | 140/123.5 |
| 5,366,461 A | 11/1994 | Blasnik | |
| 5,571,105 A | 11/1996 | Gundolf | |
| 5,722,976 A | 3/1998 | Brown | |
| 5,797,915 A | 8/1998 | Pierson, III et al. | |
| 5,807,214 A | 9/1998 | Riazi | |
| 5,810,854 A | 9/1998 | Beach | |
| 5,849,012 A | 12/1998 | Abboudi | |
| 5,972,006 A | 10/1999 | Sciaino, Jr. | |
| 6,051,007 A | 4/2000 | Hogendijk et al. | |
| 6,066,160 A | 5/2000 | Colvin et al. | |
| 6,080,185 A | 6/2000 | Johnson et al. | |
| 6,471,715 B1 | 10/2002 | Weiss | |
| 6,540,769 B1 | 4/2003 | Miller, III | |
| 6,547,725 B1 | 4/2003 | Paolitto et al. | |
| 6,589,246 B1 | 7/2003 | Hack et al. | |
| 6,648,903 B1 | 11/2003 | Pierson, III | |

(Continued)

*Primary Examiner* — Nicholas Woodall
(74) *Attorney, Agent, or Firm* — Stout, Uxa, Buyan & Mullins, LLP; Donald E. Stout (57) ABSTRACT

A surgical tensioning device for holding separated tissues in contact with one another. The device comprises a frame having two opposing first and second sides and a lower surface and an upper surface, and a band for extending around said separated tissues to be held together in conjunction with said frame. The band has two ends attached to the sides of the frame releasably. When the ends are secured to the sides of the frame, the band establishes a path of tension along its length that extends linearly between the two ends of the band.

20 Claims, 8 Drawing Sheets

(56) References Cited

U.S. PATENT DOCUMENTS

| | | |
|---|---|---|
| 6,969,398 B2 | 11/2005 | Stevens et al. |
| 6,997,189 B2 | 2/2006 | Biggs et al. |
| 7,108,710 B2 | 9/2006 | Anderson |
| 7,341,558 B2 | 3/2008 | de la Torre et al. |
| 7,416,556 B2 | 8/2008 | Jackson |
| 7,722,632 B2 | 5/2010 | Rothstein et al. |
| 7,867,251 B2 | 1/2011 | Colleran et al. |
| 7,867,253 B2 | 1/2011 | McMichael et al. |
| 2002/0147449 A1 | 10/2002 | Yun |
| 2003/0093117 A1 | 5/2003 | Saadat |
| 2005/0075653 A1 | 4/2005 | Saadat et al. |
| 2005/0090827 A1 | 4/2005 | Gedebou |
| 2005/0149121 A1 | 7/2005 | Crombie et al. |
| 2005/0240203 A1 | 10/2005 | Fuseri et al. |
| 2005/0251209 A1 | 11/2005 | Saadat et al. |
| 2007/0073289 A1 | 3/2007 | Kwak et al. |
| 2007/0112385 A1 | 5/2007 | Conlon |
| 2007/0213725 A1 | 9/2007 | Hack |
| 2007/0276437 A1 | 11/2007 | Call et al. |
| 2007/0293863 A1 | 12/2007 | Reimels et al. |
| 2007/0293864 A1 | 12/2007 | Reimels et al. |
| 2008/0004624 A1 | 1/2008 | Olroyd |
| 2008/0015589 A1 | 1/2008 | Hack |
| 2009/0062853 A1 | 3/2009 | McMichael et al. |

\* cited by examiner

SUTURE BAND BUCKLE AND METHODS

This application claims the benefit under 35 U.S.C. 119(e) of the filing date of Provisional U.S. Application Ser. No. 61/187,846, entitled Suture Band Buckle, filed on Jun. 17, 2009, and expressly incorporated herein by reference, in its entirety. This application is also related to co-pending and commonly assigned U.S. patent application Ser. No. 12/347,821, entitled Dynamic Suture Tensioning Device, filed Dec. 31, 2008, Ser. No. 12/406,902, entitled Knotless Dynamic Suture Tensioning Device and Methods, filed on Mar. 18, 2009, Ser. No. 12/406,904, entitled Load Shaping for Dynamic Tensioning Mechanisms and Methods, filed Mar. 18, 2009, Ser. No. 12/406,909, entitled Dynamic Tissue Holding Device with Low Profile Spring, filed on Mar. 18, 2009, Ser. No. 12/836,000, entitled Flat Suture Banding System and Methods, filed on Jul. 14, 2010, and Ser. No. 12/858,332, entitled Low Friction Buckle Tightening Systems and Methods, filed Aug. 17, 2010. All of the foregoing applications are expressly incorporated herein by reference, in their entirety.

BACKGROUND OF THE INVENTION

The present invention is related to the general surgical repair of separated body tissues, and more particularly to internally fixating and stabilizing such body tissues, specifically bones.

In the present state of the art, there are a number of systems available to repair biological tissues separated in surgery or by injury. These products serve to approximate and stabilize the tissues so that healing may commence and provide compression in the interface to promote healing. Compression and stability are critical for proper anatomical healing of tissue. With the correct amount of compression applied to the interface of the tissue portions to be joined, signals are sent to the tissue, thus allowing the tissue to remodel in proper anatomical position. The amount of compression applied to the tissue interface needs to be appropriate to the type of tissue that is being healed.

Twisted wires are also typically used to keep bone fragments together so they may heal. Twisted wires only hold tension as long as the twisted wire pair remains stable. Often the wires untwist too soon failing to keep the bone fragments together so that they may heal. Wires can also cut into the bone fragments allowing them to separate so that healing is difficult.

When it is necessary to access the thoracic cavity for a medical procedure, for example, it is required to cut the sternum into two pieces using a sternal saw. Once the procedure is completed within the thoracic cavity, the sternum must be repaired. For such repairs, it is known to use a dynamic compression device. Some of the drawbacks of this typical device, and others which are used include:

1. Bulky spring materials, while occupying substantial space, often do not store much energy. Some use polymer elastic bands, while other use coiled springs;

2. Wires are sometimes used to wrap the bones into position in compression with one another. However, wires can have sharp ends that can damage adjunctive tissues. Knot stacks in suture can interfere with the natural movement of surrounding tissues; and 3. Current banding systems that incorporate a biasing mechanism to achieve dynamic compression put the biasing mechanism in line with the band or suture. This practice competes with precious space at the healing site. Suture or bands are used to approximate tissues so that they may heal.

It is desirable to obtain the best purchase possible on the tissue, so that the binding mechanics offered by the suture may be utilised. The best purchase is optimized by ensuring that the suture has the greatest contact area with the tissue. If a biasing mechanism is interfering with this concept, the biasing mechanism may diminish the suture's ability to hold the tissues together.

In addition, the current banding systems have stiff bands that are not compliant with bony undulations. Flat sutures are used, but are tedious to tie and do not hold reliably.

What is needed, therefore, are improved devices and techniques for holding two tissue portions in a state of compression and tension that address and overcome these shortcomings in an innovative way.

The banding systems of the present invention are therefore attractive for use in sternal closure because they offer some distinct advantages over the twisted wires most commonly used in the procedure.

Bands address the issues wires have in the following discussion. A band, by definition, is wide. In being wide, a band distributes its forces over a wider surface area. This inhibits the band from digging into the bone. In being wide, a band affords a larger cross-sectional area whereby more material may be realized thus presenting the opportunity to offer as much strength in the construct as is necessary to hold the bone fragments together. As such, bands address wire's two main weaknesses, namely, digging into the bone fragments being held together and, not having sufficient cross sectional area.

Bands bring in other attributes other than strength and reduced pressure on the bone. Some of these attributes are difficult to manage. With strength comes stiffness, as mentioned elsewhere herein. The larger cross-section of the band significantly increases the stiffness of the band. While stiffness and rigidity are good attributes in that they can stabilize the bone union, these attributes can also prevent the band from following the contours of the bone when inserted. This can lead to capturing tissues underneath the band that ultimately destabilize the union as the tissues continue to compress and disappear over time.

Binding the band ends together can also impose some problems. Generally this involves a mechanism on one band end that interfaces with holes or slots or contours on the other band end. This creates a tensioning system that is incremental in nature. As in the twisted wire system, this mechanical interface of the two ends is the weakest link in the system. This mechanical interface becomes stronger as the incremental steps become larger. But larger incremental steps aren't conducive to fine tuning the tension, so this is problematic. Flat sutures have been used to tie tissues together but the residual tension supplied in such a knotted structure is insufficient for optimum healing. There is a lot of fuss/time associated with trying to keep and hold a desirable tension with these flat sutures. What is needed is an attachment means that provides variable tensioning.

Another problem associated with all banding systems is that they tension by pulling asymmetrically to one side requiring constant recentering while tensioning the band. What is needed therefore is a banding system with the ability to tension symmetrically without requiring recentering of the band.

The present invention addresses one or more of the issues discussed above.

SUMMARY OF THE INVENTION

The present invention pertains to a surgical tensioning device for holding separated tissues in contact with one another.

The present devices comprise a frame or buckle. The frame has two opposing first and second sides and a lower surface and/or lower side and an upper surface and/or upper side. The lower surface and/or lower side of the frame is the surface and/or side that is in contact with the tissue(s) being held together. In one embodiment, the two opposing first sides of the frame may be parallel to one another. The device further comprises a suture or band for extending around the separated tissues to be held together in conjunction with said frame. The suture or band has a first end, that is preferably attached or secured to the first side of the frame and a second end that is releasably securable to the second side of the frame. Thus, when the second end of the band is secured to the second side of said frame, the band establishes a path of tension along its length that extends linearly between the two ends of the band. In one embodiment, the band is sufficiently flexible to provide tension along its length. In yet another embodiment, the band or suture is substantially flat. Also, independently, in one embodiment, a needle may be secured to the second end of the band or suture of the device. Preferably, the frame or buckle has an opening that is sized appropriately to allow the passage of a needle that is secured to an end of the band or suture. In addition, the surfaces of the frame, for example, the surfaces of the interior of the frame, are adapted to guide the band so that the band can be easily threaded into the frame or buckle. As discussed below, the surface of the bar and corresponding mating surface on the frame may be textured or roughened for holding the band more securely once tensioned.

In one embodiment, the present device further comprises a bar or pin that is moveably attached to the second side of the frame via an attachment. The bar or pin and bar attachment are adapted to hold tension across the suture or band by pinching the second band end between the bar and the second frame side. The bar attachment is adapted to mechanically constrain movement of the bar into the inside of the frame and away from the upper surface about the second side of frame. In addition, when the bar or pin has a circular cross section, the bar attachment is adapted to prevent rotational movement of the bar once it has been engaged to pinch the second band end between itself and the second frame side.

In one embodiment, the bar is attached outside the second side of the frame via the bar attachment. In this embodiment, the bar attachment is adapted to mechanically constrain movement of the bar into the inside of the frame and away from the upper surface about the second side of frame. The bar can have any profile. In one embodiment, its profile is round, that is, it has a circular cross section. In the embodiment where the bar has a circular cross section, the bar attachment is adapted to prevent, in addition, rotational movement of the bar. Further, in this embodiment, the space between the first and second sides of the frame and the space between the bar and the outside of the second side may be substantially similar and sized to allow said band to pass through easily. Further, and independently, the surfaces of the bar and the outside of the second side of the frame, that is the mating surface for the bar, may be textured or roughened to provide improved performance, that is, to secure the second end of the band better relative to when the surfaces are not textured, once the band is tensioned.

In accordance with the device described above, when the second band end is routed around and through tissues being held together and from the bottom up through the center of the frame and over the second frame side and down between the second frame side and bar such that when second band end is tensioned and released, the bar holds the tension by pinching the band between the bar and second frame side.

In another embodiment, the bar is attached inside the frame at the second side of the frame via the bar attachment. In this embodiment, preferably, a support or buttress is provided inside the frame at the second frame side that includes an upper cam surface. The bar is attached at the second frame side, via a bar attachment, to the support on the upper cam surface of the support, so that the upper cam surface is contiguous with the upper surface of the frame at the second side of the frame. In this embodiment, the bar attachment is adapted to mechanically constrain movement of the bar into the inside of said frame and away from the upper surface of the frame and away from the support about the second side of frame. The bar can have any profile. In one embodiment, its profile is round, that is, it has a circular cross section. In the embodiment where the bar has a circular cross section, the bar attachment is adapted to prevent, in addition, rotational movement of the bar. The cam surface allows for supplying more leverage to the hinging attachment mechanism such that the bar can be forced harder into and be better locked inside the upper cam surface of the support against the second frame side. Further, in this embodiment, the space between the bar and the inside of the first side of the frame and the space between the bar and the inside of the second side are substantially similar and are sized to allow suture or band to pass through easily. Further and independently, the surfaces of the bar and the inside of the second side of the frame, that is the mating surface for the bar, may be textured or roughened to provide improved performance, that is, to secure the second end of the band better relative to then the surfaces are not textured, once the band is tensioned. In the embodiment of the device where a needle is attached to the second end of the band, the bar is adapted to move away from the second frame side to a sufficient distance so as to allow the needle to pass around the bar.

In accordance with the device described above, when the second band end is routed around and through tissues being held together and from the bottom up through the center of the frame and over the bar and down between the bar and second side of frame such that when second band end is tensioned and released, the bar holds said tension by pinching the band between the bar and second frame side.

In accordance with yet another embodiment of the present device is described a surgical tensioning device for holding separated tissues in contact with one another wherein the device comprises a frame with two opposing first and second sides, which are preferably parallel to each other, and a lower surface and/or lower side and an upper surface and/or upper side. The lower surface and/or lower side is the surface and/or side that is in contact with the tissue(s) being held together. The device further comprises a band or suture for extending around the separated tissues to be held together in conjunction with the frame. The band in this embodiment has a first end that is releasably securable to the first side of the frame and, a second end that is releasably securable to the second side of said frame. When the first and second ends are secured to both first and second sides of the frame, the band establishes a path of tension along its length. In addition, the band or suture is tensioned evenly utilising the two ends of the band without requiring repositioning of said frame once positioned. Such tensioning is accomplished as follows. The device comprises a first bar or pin that is moveably attached to and preferably, parallel to, the first frame side via bar attachments and, a second bar that is moveably attached to and preferably, parallel to, the second frame side via bar attachments. The first and second bars and the respective attachments are adapted to hold the tension across the suture or band by pinching the first and second band ends between the first bar and the first frame side and the second bar and the second frame side, respectively.

In the device described above, the first and second bars may be secured to their respective frame sides either inside or outside the frame.

In accordance with yet another embodiment of the invention is described a needle guide, adapted to be used in conjunction with any of the devices described above. The purpose of the needle guide is to mitigate or prevent any damage to the bars and attachments of the devices when a large needle of the kind used in these surgical repairs is used. The frame or buckle of the present devices has been designed to be small because this is a desirable quality for orthopedic implants. The needle used in these surgical repairs needs to be abnormally large so that it can pierce sternal bone. Sternal needles therefore are some of the largest needles made for threading sutures. The present needle guide removably fits or attaches to the frames of the present devices. The needle guide comprises slots, preferably integral slots so that the needle guide and slots are a single element, and is sized to fit via the slots over the bar in order to restrain the bar which, when placed over the bar, mitigates or prevents damage to the bar and bar attachment from the.

Once the frame of the present devices has been threaded with the suture and the bar(s) is set, the needle guide may be removed as it has no further function. This is desirable as this lowers the profile of the implant.

As used herein, the tissue portions to be held in contact with one another in the present invention comprise biological tissue in the body, including, but not limited to, skin, tendon, bone, ligaments, blood vessels, and organs. In one embodiment, the tissue portions comprise sternal bone that has been cut for a procedure to access the thoracic cavity.

The dermal layer on top of the sternum is rather thin. Even when a surgeon employs only twisted wire to repair the sternum, some patients can feel that wire under their skin. Consequently, the profile of a closure device can have cosmetic as well as practical concerns. The dermal layer over the sternum on an average adult female is 5 to 10 mm thick. A device that is ~5 mm in height is sufficiently thick to be rather clearly seen in some adults. The profiles of the current inventive devices are spread out over a large surface area, resulting in a much more favorable aspect ratio, it will not be easily seen when viewing the patient from the outside.

A particularly advantageous feature of the invention is that the aspect ratio of the inventive device, defined as the height of the device above the tissue surface, divided by the length of the device, is less than or equal to approximately 0.50, and more preferably approximately 0.10. In addition, the maximum height or profile of the current inventive device at the frame preferably is about 4 mm to about 1 mm.

In certain preferred embodiments, the buckle or frame of the device is fabricated from either tempered stainless steel, spring tempered stainless steel or titanium.

In certain preferred embodiments of the present invention, the pins or bars of the device are fabricated from either tempered stainless steel, spring tempered stainless steel or titanium.

In certain preferred embodiments of the present invention, attachments or straps of the device are fabricated from either spring tempered stainless steel or titanium.

In one embodiment, the band or suture of the present devices is sufficiently flexible to provide tension along its length. In yet another embodiment, the band or suture is substantially flat. The suture or band may be defined by that which is normally available. It may be woven fibers or a monofilament and can be any material. Accordingly, the band may comprise woven, braided, or knitted fibers or metals, or a monofilament, and can be made of any known suture material. The suture may be of any shape, including, but not limited to, round, square, oval, flat (like a strap), or tubular. The shape of the suture or band for particular embodiments will be discussed more fully herein below. In one embodiment of the inventive device, the suture preferably comprises flat or tape suture.

On one end of the suture or band may be a needle or other receptacle to facilitate stitching or weaving in tissue or bone. Accordingly, in one embodiment, a needle may be secured to the second end of the band or suture of the device. Alternately, a needle may be secured to both ends of the suture.

The invention, together with additional features and advantages thereof, may best be understood by reference to the following description taken in conjunction with the accompanying illustrative drawings.

DESCRIPTION OF THE PREFERRED EMBODIMENTS

Figure 1:
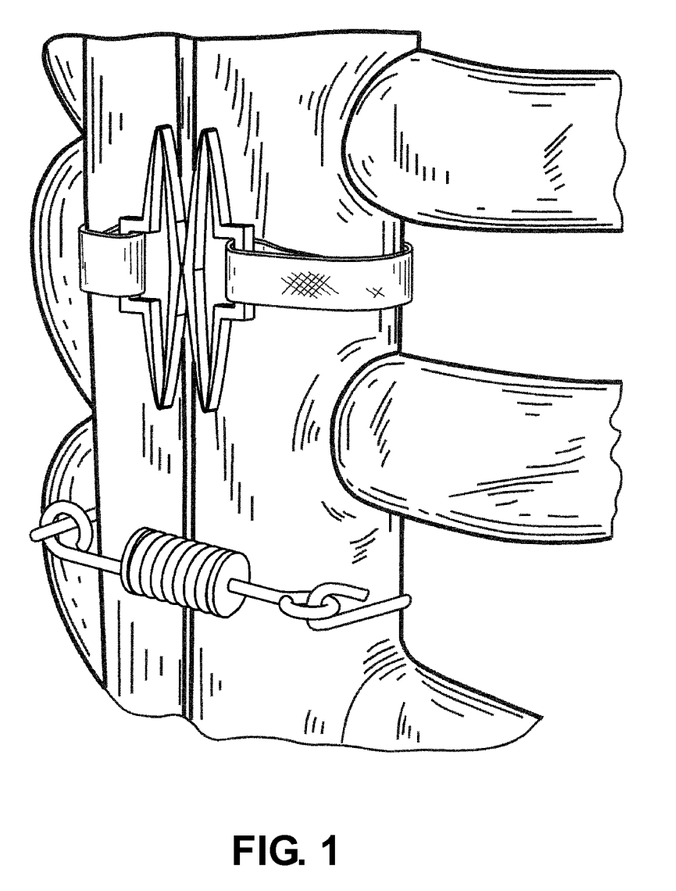
FIG. 1 is a top view showing how wires and bands might be used in binding sternal halves together for healing after open heart surgery.

Referring now more particularly to the drawings, there is shown in FIG. 1 how wires and bands might be used in binding sternal halves together for healing after open heart surgery.

Figures 2, 2B:
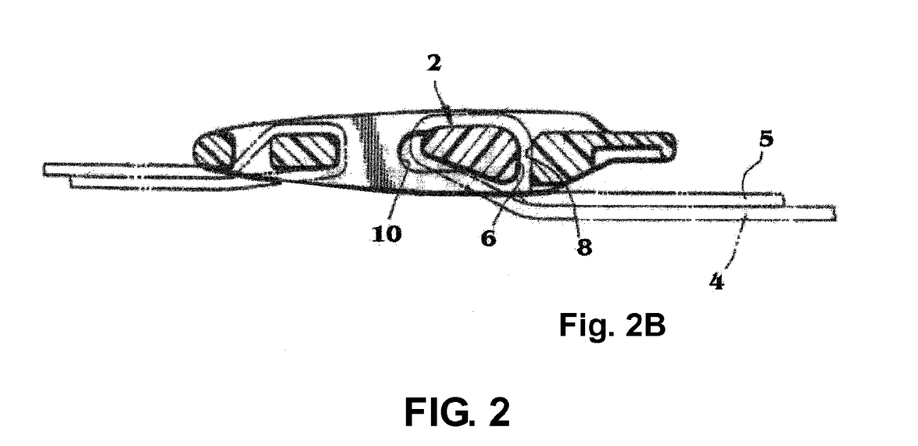
FIG. 2B is a cross sectional view of the buckle in FIG. 2A used with a strap.
Figure 2A:
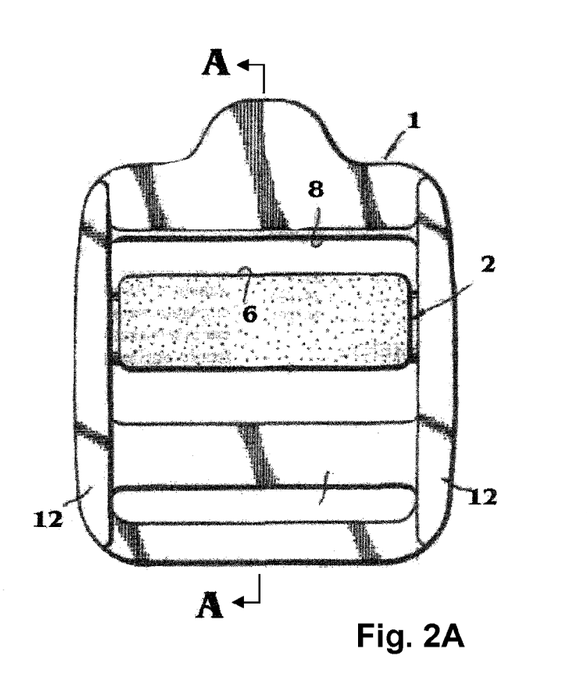
FIG. 2A is a top view of a common buckle.

A strap locking system similar with a common buckle 1 is represented in FIG. 2. Referring to FIGS. 2A and 2B, a common buckle 1, used in straps on bags might be considered in this application for its variable tensioning abilities. Lock bar 2 moves surface 6 away from surface 8 when strap tail 5 is tensioned. As strap tail 5 is tensioned, strap tail 4 is pulled into the 6/8 surface interface. When strap tail 5 is released, strap tail 4 holds the dominate tension which pulls lock bar 2 so that the strap is pinched between surfaces 6 and 8. This is the locked position of the buckle 1. Locking bar 2 is held in position by tabs on both if its ends that ride in slot 10 which is cut out of frame 12. Slot 10 is critical in the operation because it holds face 6 on locking bar 2 so that it correctly pinches the strap up against surface 8. The variability of the tensions in strap tails 4 and 5 cause the lock bar to move in slot 10. The lock bar naturally wants to even out these tensions by rotating in slot 10. Flats are milled in the lock bar 2 ends to ride in slot 10 so that such rotation does not happen.

This buckle generally has the means to provide variable tensioning to the strap loop. However with a suturing system, it is necessary to have one of these strap ends free so that it may be routed through tissue with a common suture-end-needle arrangement.

This common buckle 1 comes pre-threaded. What would be needed to make a buckle suitable for a suture application is to have the buckle designed so that it might be threaded by the surgeon. In its common configuration, there is not enough room around locking bar 2 to fit a suture needle.

The distance locking bar 2 has to travel to achieve this locking and unlocking is rather small. So slot 10 provided for locking bar ends are not long. Should this be scaled down to the size of a 5 mm wide suture band, the slot only needs to be 0.020 inches long. As thus, the slot does not provide bar travel sufficient to allow a common needle, 0.065 inches in diameter, to be threaded through the buckle. Furthermore, it would be difficult to make this common buckle design open up enough to make such threading easy. Surgeons would like to see an obvious opening for the needle to pass through.

Figures 3, 3B:
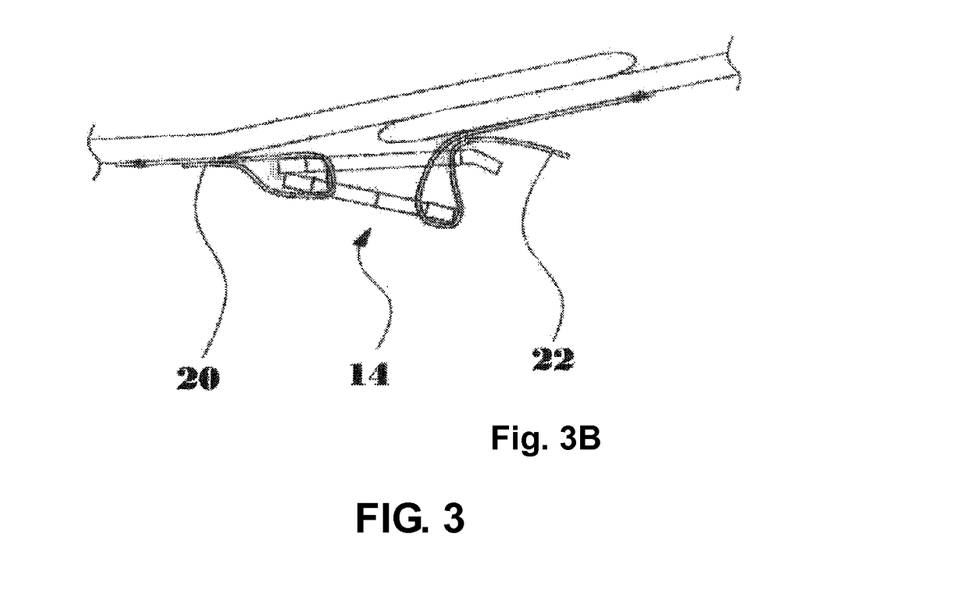
FIG. 3B is a cross sectional view of the buckle in FIG. 3A used with a strap.
Figure 3A:
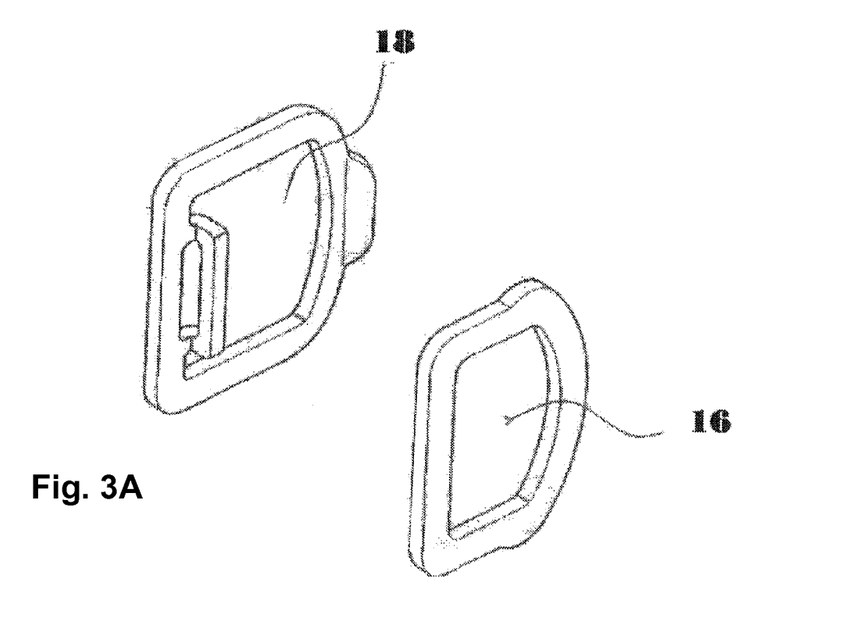
FIG. 3A is a perspective view of plates used in a common buckle.

A strap locking system similar to common buckle 2 is represented in FIG. 3. This system 14 shown in FIG. 3A consists of two plates 16 and 18 that are joined by strap loop 20 (shown in FIG. 3B) at one end. Plate 16 is made smaller than plate 18 so that strap end 22 is pinched between adjoining surfaces on plates 16 and 18 when threaded as shown in FIG. 3B and then tensioned. The locking difference between plate system 14 and common buckle 1 lays in the pinching mechanism. Plate system 14 moves plate 16 on a hinge to lock and release strap 22. Plate 16 can only lay parallel to plate 18 and thus the surfaces on the locking mechanism are confined to plate surfaces as managed by the hinging action. These constraints limit the effectiveness of plate system 14's locking abilities. The pinching surfaces are commonly only lines. Common buckle 1 can have any approach to the pinching system as defined by slot 10 and pinching surfaces 6 and 8 can be of any shape. Strap locking system 14 is interesting because it can be easily threaded by a suture-needle construct.

Figure 4:
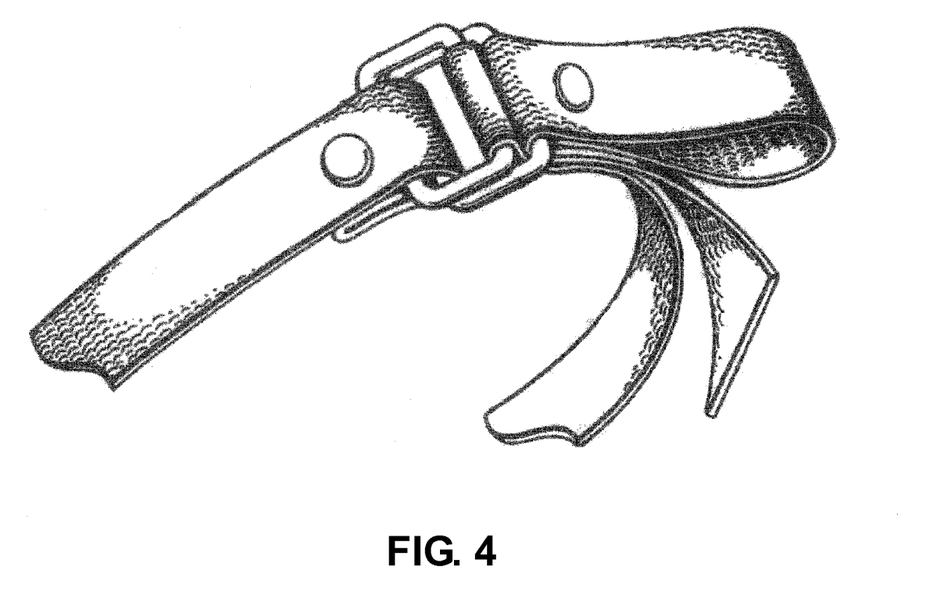
FIG. 4 is a perspective view of a buckle design where wires are used instead of plates.

FIG. 4 shows a similar buckle design as in FIG. 3 where wires are used instead of plates. The pinching surfaces are only opposing lines on either wire. As with the plate system 14, this wire buckle system may be threaded with the loose strap end. This works fine as long as the buckle is big enough to be manipulated with fingers. But when the buckle gets small on the scale of a 5 mm tape suture, the buckle becomes too small to manipulate for threading.

The present invention is directed to a strap buckle that can be threaded, has good strength holding characteristics, and is small so as to be used with suture sized straps. Furthermore, the present invention provides for holding the buckle open so that it may be easily threaded by a needle/suture construct.

The tissue portions to be held in contact with one another in the present invention comprise biological tissue in the body, including, but not limited to, skin, tendon, bone, ligaments, blood vessels, and organs. In one embodiment, the tissue portions comprise sternal bone that has been cut for a procedure to access the thoracic cavity. The suture may comprise woven, braided, or knitted fibers or metals, or a monofilament, and can be made of any known suture material. The suture may be of any shape, including, but not limited to, round, square, oval, flat (like a strap), or tubular. The shape of the suture for particular embodiments will be discussed more fully hereinbelow. In one embodiment of the inventive device, the suture preferably comprises flat or tape suture.

In certain preferred embodiments, the buckle or frame of the device is fabricated from either tempered stainless steel, spring tempered stainless steel or titanium.

Figure 5A:
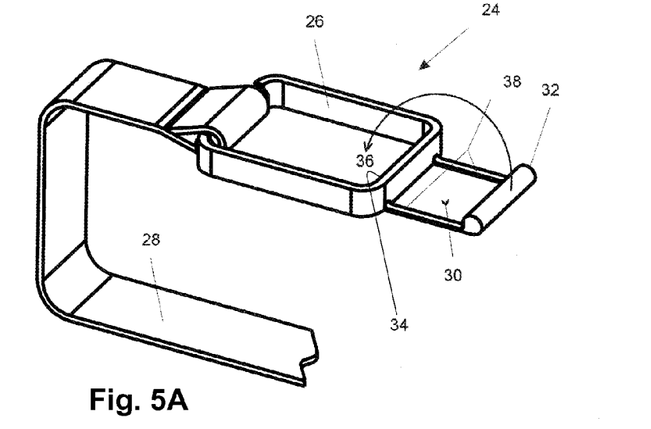
FIG. 5A is a perspective view of a portion of suture band buckle in accordance with an embodiment of the present invention wherein the fixed suture at one end of the buckle is shown.
Figure 5B:
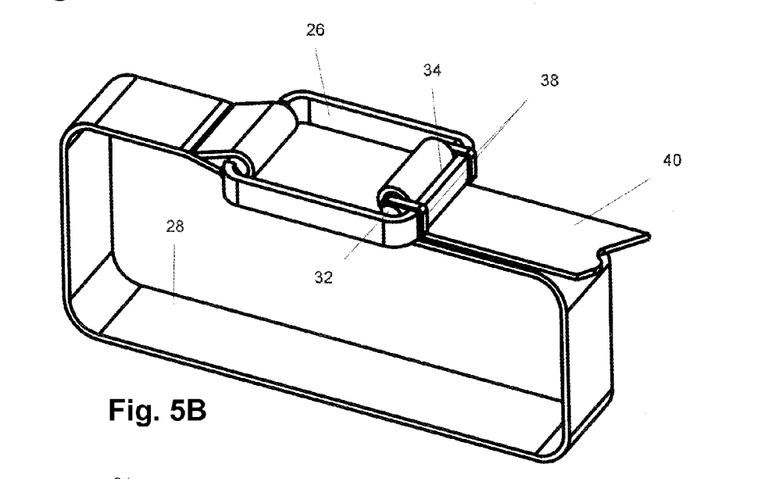
FIG. 5B is a perspective view of the suture band buckle shown in FIG. 5A with the suture at the both ends of the buckle shown.
Figure 5C:
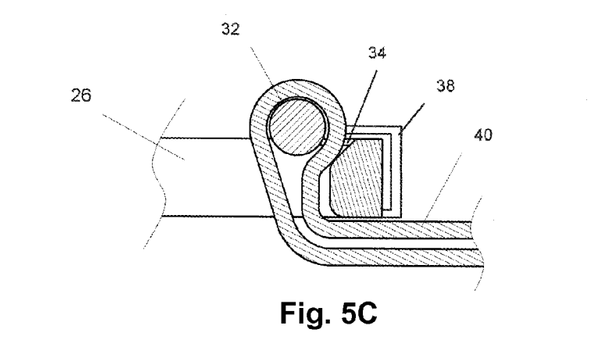
FIG. 5C is a cross sectional view of the buckle in FIG. 5A into which the loose end of suture has been secured.

FIG. 5 represents one embodiment of the invention. As shown in FIGS. 5A and 5B, buckle 24 consists of frame 26 with a member 32 linked via attachments 38 to frame 26. The member 32 is in the form of a pin or bar in this embodiment. In addition, the member 32 may be rigid. Attachments 38 are in the form of straps in this embodiment. These attachment members that link the rigid pin or bar 32 to the frame 26, are preferably constructed to yield to slight pressure and form around frame 26. Pin or bar 32 ultimately pinches the suture up against the inside surface 34 of frame 26. One tail of suture or band 28, the first end, comes attached to the frame in this embodiment. The other tail or second end of the suture or band 28 is easily threaded into buckle 24 through window 30 held open by attachment straps 38. As tension is applied to suture tail 40, the pin or bar 32 rotates in direction 36 to go from the outside of frame 26 to the inside of frame 26. Attachment straps 38 yield and form around frame 26 in this process. The straps serve to hold the pin in proper position to pinch the suture against inside surface 34 when tension is released on suture tail 40. Straps 38 also keep the bar or pin 32 from rotating. All though round bars or pins are shown up against flat surfaces in this embodiment, contoured pins with contoured mating surfaces on the pin and frame respectively, may be used to increase the buckle's holding performance. The mating surfaces, contoured or otherwise, may be further roughened or textured if more performance or better grip or holding is required.

In certain preferred embodiments of the present invention, the pins or bars of the device are fabricated from either tempered stainless steel, spring tempered stainless steel or titanium.

In certain preferred embodiments of the present invention, attachments or straps of the device are fabricated from either spring tempered stainless steel or titanium.

Buckle 24 has attachment straps 38 that perform the same function as slot 10 does in buckle 1 yet buckle 24 is simple enough to allow the free second end of suture 40 to be threaded through the buckle. Attachment straps 38 provide the same two functions slot 10 does in buckle 1; first to guide the pin into its mating locking inside surface 34, and second to keep the pin or bar 32 from rotating in the lock. Attachment straps 38 also hold a window open to allow the threading of free suture end 40. All though the buckles represented in FIGS. 3 and 4 are capable of being threaded, it would be difficult to manage with gloved fingers on such a small scale. This is all done in a low profile device as is required for such surgical implants. A downsized version of buckle 1 would have a larger profile due to the material needed around the slots.

Figure 6A:
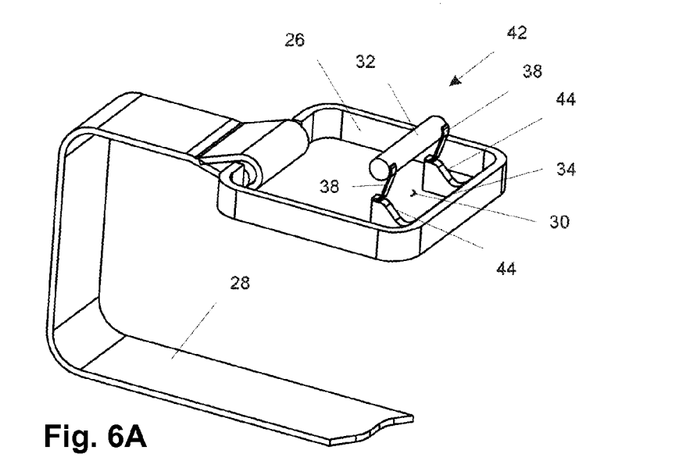
FIG. 6A is a perspective view of a portion of suture band buckle in accordance with an embodiment of the present invention wherein the fixed suture at one end of the buckle is shown.
Figure 6B:
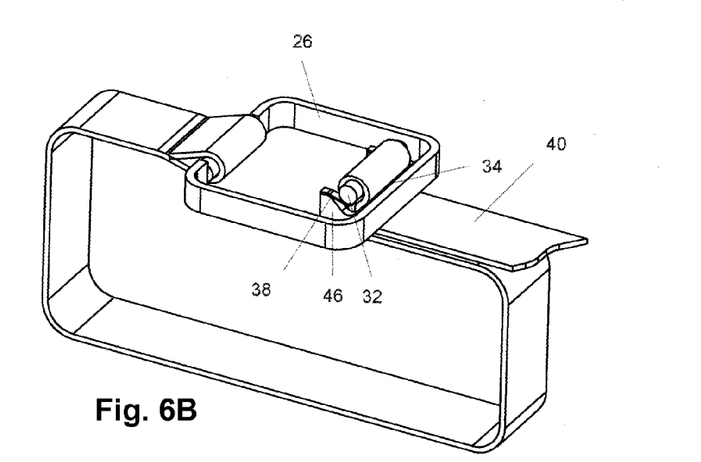
FIG. 6B is a perspective view of the suture band buckle shown in FIG. 6A with the suture at the both ends of the buckle shown.
Figure 6C:
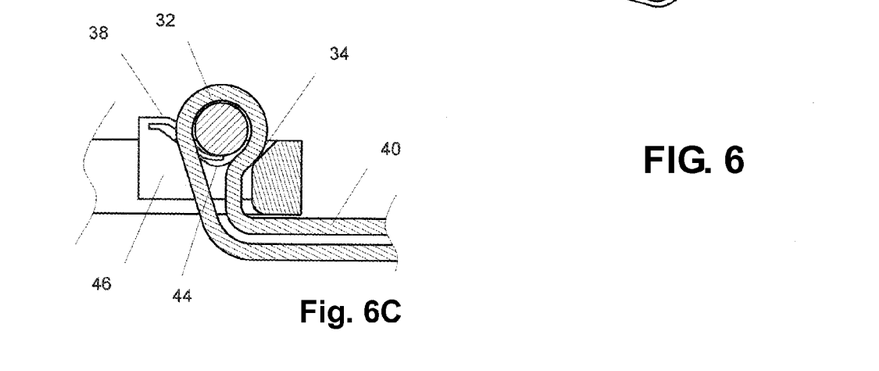
FIG. 6C is a cross sectional view of the buckle into which the loose end of suture has been secured.

FIG. 6 presents another embodiment of the present invention with buckle 42 which is similar to the embodiment in FIG. 5 in that it has the same frame 26 and bar or pin 32 and attachment straps 38. Straps 38, however, start in the interior of the frame instead of outside the frame. This is managed by placing buttress 46 on the interior of the frame and supplying a cam surface 44 to aid the straps in guiding bar or pin 32. Consequently space 30 is supplied inside the frame for threading loose suture end 40. All the same advantages are realized with buckle 42 as buckle 24. Buckle 42 has the additional advantage of having a simple threading route whereas buckle 24's threading route is a bit more complicated.

The cam surface 44 and strap 38 combination provide the same two functions slot 10 does in FIG. 2; first to guide the pin into its mating locking inside surface 34, and second to keep pin 32 from rotating in the lock. Cam surface 44 has the additional advantage of supplying more leverage to the hinging strap mechanism such that pin 32 is forced harder into and better locked inside surface 34. All though round bars or pins are shown in this embodiment, contoured pins with contoured mating surfaces on the pin and frame respectively, may be used to increase the buckle's holding performance. The mating surfaces, contoured or otherwise, may be further roughened or textured if more performance or better grip or holding is required.

The design criterion for this invention is to present an easily threaded buckle to the physician. Thus far, this has been managed by opening up the buckle's architecture to allow for the suture to be threaded around pin 32. Due to the size of pin 32 and straps 38, the large needle needed for these procedures could easily push and bend pin 32 and straps 38 so they do not function optimally. What is needed is something that can both guide the needle around pin 32 and hold pin 32 so that the needle is not prone to disturb pin 32 and strap 38's functionality. Such a guide should facilitate the two passes the needle needs to make to route suture 28 around pin 32. The first pass comes up from the bottom and is the most difficult to manage as the needle is hard to see underneath the buckle. The second pass is easier to see as it originates from the top of buckle 42.

Figures 7, 7A, 7B:
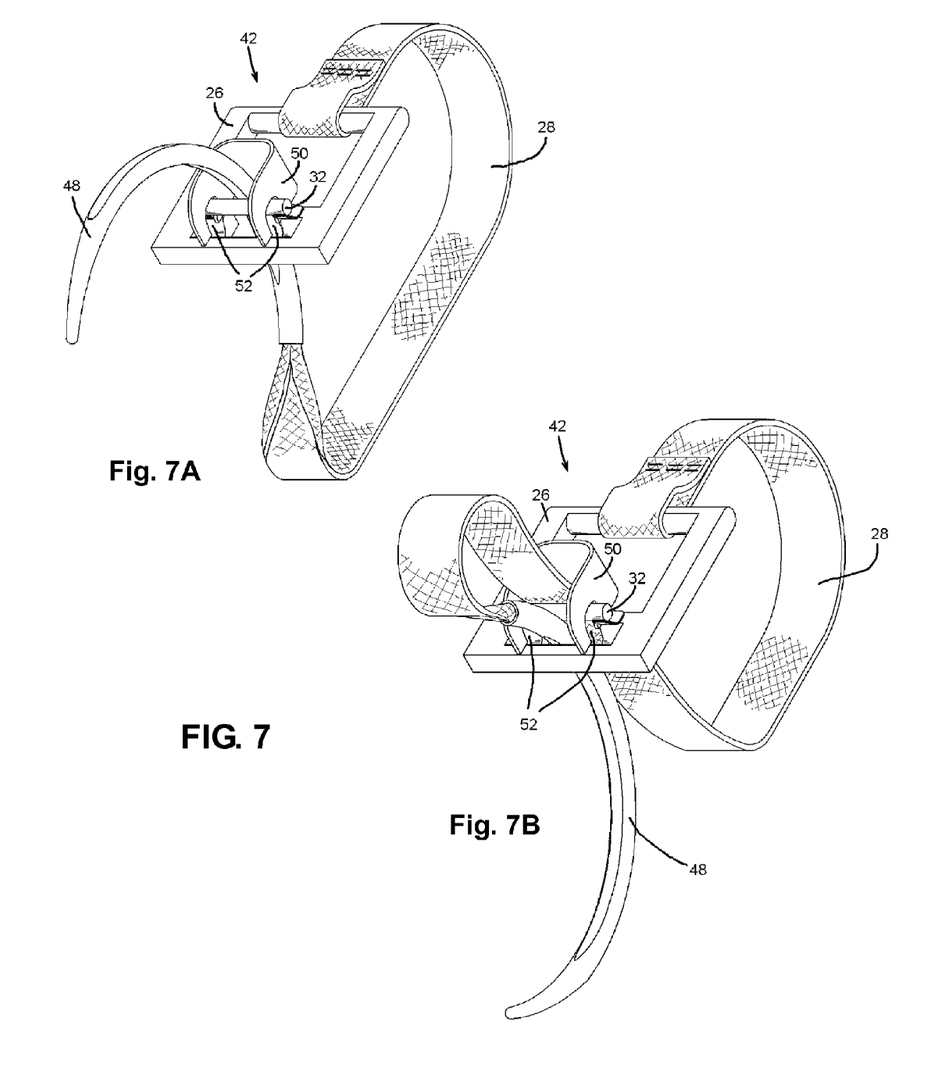
FIG. 7 is a perspective view of a suture band buckle in accordance with an embodiment of the present invention, with suture and a needle attached to the suture and, a needle guide in accordance with an embodiment of the present invention.
FIG. 7A shows the needle being guided by the needle guide into the buckle.
FIG. 7B shows the suture and needle being guided out of the buckle.

FIG. 7 shows a design development of buckle 42 that presents a clear path with which needle 48 is guided around pin 32 by means of guide 50. FIG. 7A shows needle 48 in this path on the way up behind pin 32. The inner surface of guide 50 serves to provide this path behind pin 32 which is the harder of the two needle passes to manage as the needle comes up blind, underneath buckle 42. The needle tip needs to find the interior of guide 50 and then can slide along this surface without disturbing pin 32. Should needle 48 accidently hit pin 32, slots 52 in guide 50 restrain pin 32's movement so that damage is not realized to pin 32.

FIG. 7B shows needle 48 on its way down in front of pin 32. In this configuration, visualization is much better. But still, there can be miscalculations in needle 48 movement that damage pin 32. Guide 50 mitigates or prevents this again with integral slots 52 which serve to restrain pin 32 such that damage to pin 32 or straps 38 is not realized.

Buckle 42 has been designed to be small because this is a desirable quality for orthopedic implants. Needle 48 needs to be abnormally large so that it can pierce sternal bone. Sternal needles are some of the largest needles made for threading sutures. While guide 50 is effective in guiding needle 48 around pin 32, it does not provide enough room to accommodate the large sternal needle 48. The present invention addresses this issue in the design of slots 52. Slots 52 in guide 50 are widened to allow lateral movement of pin 32 within the slot. This allows some of the space within guide 50 to be utilized for both the upward and downward passes of needle 48.

Guide 50 is a removable element releasably attached to frame 26. Once buckle 42 is threaded and locking pin 32 is set, guide 50 may be removed as it has no further function. This is desirable as this lowers the profile of the implant.

It is now evident that the present invention has created a buckle that is both easy to thread yet has a superior holding power. In miniaturizing the design, the buckle has been further modified with a needle guide to facilitate threading the buckle with larger needles.

Figure 8:
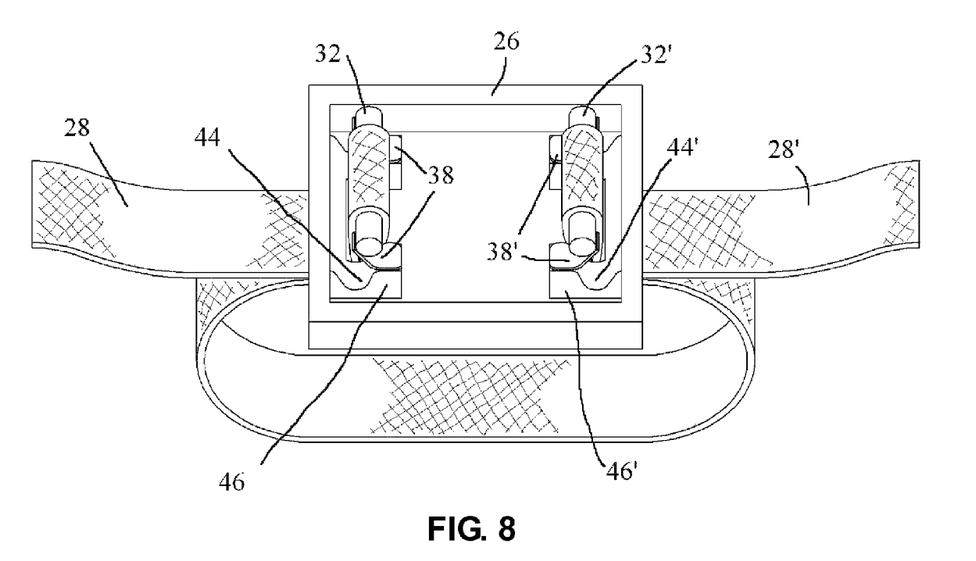
FIG. 8 is an isometric view of a suture band buckle in accordance with an embodiment of the present invention, into which two loose ends of suture have been secured.

It is common, in surgical procedures, to work in tight spaces that require a small vertical access to the buckle. The present invention has one buckle on frame 26 with which to tighten suture 28. When the suture 28's tail or end is pulled to tighten the repair, the frame 26 can be pulled off to the side. This is not acceptable, and frame 26 must be re-centered on the repair before tensioning proceeds. After centering frame 26, tensioning proceeds but immediately pulls frame 26 off to the side again. This pulling and centering becomes a tedious process that has an easy remedy. As a remedy, described herein is one embodiment, shown in FIG. 8, that has two opposed sets of locking members in the form of bars or pins 32 and 32' with related locking mechanisms using straps 38 and 38' on frame 26 so that the two opposing suture tails or ends can be pulled in unison and secured by the respective bars or pins 32 and 32' on frame 26 thus keeping the implant on center. As shown in FIG. 8, the bars or pins 32 and 32' can be disposed inside the frame in a similar fashion as shown in FIGS. 6 and 7, with buttresses 46 and 46' on the interior of the frame and supplying cam surfaces 44 and 44' to aid the straps 38 and 38' in guiding bars or pins 32 and 32'. In an alternate embodiment, the bars or pins 32 and 32' can be disposed outside the frame in a similar fashion as shown in FIG. 5 (this embodiment is not shown). In a preferred embodiment, the bars or pins 32 and 32' and the attachments 38 and 38', respectively, are substantially identical except that they are disposed on opposite sides of frame 26.

While the inventive concept is disclosed as being particularly adapted for use in repairing the sternum after a thoracic cavity procedure, it is, of course, applicable to a great many other procedures requiring repair of bodily tissue, particularly bone.

Accordingly, although exemplary embodiments of the invention have been shown and described, it is to be understood that all the terms used herein are descriptive rather than limiting, and that many changes, modifications, and substitutions may be made by one having ordinary skill in the art without departing from the spirit and scope of the invention, which is to be limited only in accordance with the following claims.

What is claimed is:

1. A surgical tensioning device for holding separated tissues in contact with one another, the device comprising:
    a frame, said frame having two opposing first and second sides, a lower surface, and an upper surface;
    a band for extending around the separated tissues to be held together in conjunction with said frame;
    said band having a first end attached to the first side of said frame and a second end that is releasably securable to the second side of said frame, wherein, when the second end is secured to said second side of said frame, said band establishes a path of tension along its length that extends linearly between the two ends of the band; and
    a bar moveably attached to the second side of said frame via a bar attachment, said bar and attachment being adapted to hold tension by pinching said second band end between said bar and second frame side, said bar attachment comprising a plurality of attachment straps connecting the bar to the second side of the frame, wherein the attachment straps are constructed to yield to slight pressure of a level applied when tensioning the band in order to move and hold the bar in a desired orientation to clamp the band in place.

2. The device of claim 1 wherein said bar attachment is adapted to mechanically constrain movement of said bar into the inside of said frame and away from said upper surface about the second side of the frame.

3. The device of claim 1 wherein said bar is attached inside the frame at the second side via a said bar attachment that is adapted to mechanically constrain movement of said bar into the inside of said frame and away from said upper surface about the second side of frame.

4. The device of claim 3 wherein the space between the bar and the inside of the first side of said frame and the space between the bar and the inside of the second side are substantially similar and are sized to allow said band to pass through easily.

5. The device of claim 3 wherein said bar has a circular cross section and said bar attachment is adapted to constrain said bar from rotational movement.

6. The device of claim 1 wherein said bar is attached outside the second side of said frame via a said bar attachment that is adapted to mechanically constrain movement of said bar into the inside of said frame and away from said upper surface about the second side of the frame.

7. The device of claim 6 wherein the space between the first and second sides of said frame and the space between the bar and the outside of the second side are substantially similar and are sized to allow said band to pass through easily.

8. The device of claim 6 wherein said bar has a circular cross section and said bar attachment is adapted to constrain said bar from rotational movement.

9. The device of claim 1, and further comprising a needle attached to the second end of the band.

10. The device of claim 9 wherein said frame has an opening sized to allow passage of said needle through it.

11. The device of claim 9 and further comprising a needle guide having integral slots and sized to removably fit via said slots over said bar in order to restrain said bar, wherein said needle guide is adapted to mitigate or prevent damage from said needle to said bar and bar attachment when said needle guide is placed over said bar.

12. The device of claim 3, and further comprising a needle attached to the second end of the band wherein said bar is adapted to move away from said second frame side to a sufficient distance so as to allow the needle to pass around said bar.

13. The device of claim 1 wherein said band is substantially flat.

14. The device of claim 1 wherein the height of the device at the frame is between about 4 mm and about 1 mm.

15. The device of claim 1, wherein the surfaces of said bar and the inside of said second side of said frame are textured.

16. The device of claim 1, and further comprising a buttress disposed within said frame, said buttress having a cam surface thereon for guiding said pin.

17. The surgical tensioning device as recited in claim 1, wherein said attachment straps are fabricated of spring tempered stainless steel or titanium.

18. A surgical tensioning device for holding separated tissues in contact with one another, the device comprising:
a frame, said frame having two opposing first and second sides, a lower surface, and an upper surface;
a band for extending around the separated tissues to be held together in conjunction with said frame, said band having a first end that is attached to the first side of said frame and, a second end that is releasably securable to the second side of said frame, wherein, when the second end is secured to said second sides of said frame, said band establishes a path of tension along its length and extends linearly between the two ends of the band; and
a bar moveably attached parallel to the second side of said frame via a bar attachment, said bar and attachment being adapted to hold said tension by pinching said second band end between said bar and second frame side, said bar attachment comprising a plurality of attachment straps connecting the bar to the second side of the frame, wherein the attachment straps are constructed to yield to slight pressure of a level applied when tensioning the band in order to move and hold the bar in a desired orientation to clamp the band in place.

19. The surgical tensioning device as recited in claim 18, wherein said attachment straps are fabricated of spring tempered stainless steel or titanium.

20. A surgical tensioning device for holding separated tissues in contact with one another, the device comprising:
a frame, said frame having two opposing first and second parallel sides, a lower surface, and an upper surface;
a band for extending around the separated tissues to be held together in conjunction with said frame, said band having a first end that is releasably securable to the first side of said frame and, a second end that is releasably securable to the second side of said frame, wherein, when the first and second ends are secured to both first and second parallel sides of said frame, said band establishes a path of tension along its length and tensions evenly utilizing the two ends of the band without requiring repositioning of said frame once positioned; and
a first bar moveably attached to and parallel to said first frame side via bar attachments and a second bar moveably attached to and parallel to said second frame side via bar attachments, said bars and attachments being adapted to hold said tension by pinching said first and second band ends between said first bar and said first frame side and said second bar and said second frame side, respectively, wherein each of said bar attachments comprise a plurality of attachment straps connecting the bar to which it is attached to the frame, the attachment straps being constructed to yield to slight pressure of a level applied when tensioning the band in order to move and hold the connected bar in a desired orientation to clamp the band in place.

* * * * *